United States Patent [19]

McElhany

[11] Patent Number: 5,863,496
[45] Date of Patent: Jan. 26, 1999

[54] STERILE PACKAGING

[75] Inventor: Clay R. McElhany, Portland, Oreg.

[73] Assignee: Prepared Media Laboratory, Inc., Wilsonville, Oreg.

[21] Appl. No.: 758,203

[22] Filed: Nov. 25, 1996

[51] Int. Cl.6 .............................. A61L 2/08; E65D 30/08
[52] U.S. Cl. ............................... 422/22; 422/28; 422/40; 428/35.2; 383/113
[58] Field of Search .................... 428/35.2, 913; 383/111, 113; 206/438; 220/403; 53/46, 47; 422/22, 28, 40, 36

[56] References Cited

U.S. PATENT DOCUMENTS

| | | | |
|---|---|---|---|
| 4,578,351 | 3/1986 | Rosevear et al. | 435/41 |
| 4,700,838 | 10/1987 | Falciani et al. | 206/438 |
| 4,714,595 | 12/1987 | Anthony et al. | 422/294 |
| 4,813,210 | 3/1989 | Masuda et al. | 53/425 |
| 4,863,688 | 9/1989 | Schmidt et al. | 422/28 |
| 4,910,147 | 3/1990 | Bacehowski et al. | 435/304.1 |
| 5,008,076 | 4/1991 | Johansson et al. | 422/28 |
| 5,322,161 | 6/1994 | Shichman et al. | 206/204 |
| 5,470,151 | 11/1995 | Walthall et al. | 366/165.1 |
| 5,482,684 | 1/1996 | Martens et al. | 422/119 |

*Primary Examiner*—William H. Beisner
*Assistant Examiner*—Alex Noguerda
*Attorney, Agent, or Firm*—Chernoff, Vilhauer, McClung & Stenzel, LLP

[57] ABSTRACT

A method of achieving sterile dry packaging, the key steps of which include enclosing a sterile item in one or more thin-gauge inner bags which are in turn enclosed within a polyethylene/metallized polyester laminate and sealed therein, followed by gamma irradiation and sterilization of the outer surface of the laminate with a vaporized sterilizing agent such as hydrogen peroxide.

13 Claims, No Drawings

STERILE PACKAGING

BACKGROUND OF THE INVENTION

The use of blood culture media to ascertain the presence and identity of microorganisms in medical and laboratory research applications is well known. In use, the culture medium is inoculated with, for example, a scraping from the environment or patient, incubated, and then studied for the presence of characteristic microbial growth patterns. Typically, such a protocol is carried out in a sterile "clean room." In order for the testing to be accurate, it is absolutely essential that the culture media be totally sterile prior to the test. This is generally accomplished by sterilizing the media immediately prior to the inoculation in an isolation chamber by contacting the packaging of the media with a sterilizing agent at ambient temperatures. Conventional sterilizing agents, used in vaporized mist form, are aqueous solutions of hydrogen peroxide, formaldehyde, peracetic acid, and mixtures thereof.

A major problem associated with the use of such sterilizing agents is that they are sufficiently corrosive to attack and break down and so penetrate the packaging for the culture media, thereby allowing premature exposure of the media to the environment, along with contamination of the media by the sterilizing agent. Attempts have been made to address this problem by enclosing the culture media in heavy gauge packaging material to form a vapor barrier. However, this method in turn often leads to the formation of "wet" culture media due to evaporation of water contained within the media, followed by condensation within the packaging material. The formation of moisture on culture media, even in slight amounts, is problematic in that the characteristic growth patterns of microorganisms tend to become blurred and indistinct, thereby preventing proper identification of the microorganism in question. To allow moisture to escape, semipermeable packaging material such as bonded olefin (sold by DuPont as Tyvek®) has been used, but this material is insufficiently resistant to attack by the conventional sterilizing agents mentioned above.

Clean rooms are also used for other medical and laboratory research applications, and for fabrication and handling of items that are extremely sensitive to microbial contamination. To maintain such clean rooms and equipment therein in relatively sterile condition, sterile absorbent wipes and sterilizing solutions are routinely used. However, the packaging for such wipes and solutions is itself subject to microbial contamination when it is in storage awaiting use.

There is therefore a need for packaging that is capable of maintaining a sterile item in a sterile and dry condition, while at the same time being capable of withstanding chemical attack by commonly used sterilizing agents. These needs and others are met by the present invention, which is summarized and described in detail below.

SUMMARY OF THE INVENTION

The invention comprises a process of making a sterile dry package for sterile items; the essential steps of which include enclosing the sterile item in one or more thin-gauge inner bags, the inner bags being nested within each other and then sealed within a laminate material capable of withstanding contact with vaporized sterilizing agents, followed by gamma irradiation and sterilization of the outer surface of the laminate with a vaporized sterilizing agent.

DETAILED DESCRIPTION OF THE INVENTION

According to the present invention there is provided a process of making a sterile dry package of a sterile item comprising the steps of:

placing the sterile item into at least one inner container and closing the same;

placing the closed inner container(s) into a sealable container comprising a laminate of low density polyethylene and metallized polyester and sealing the same to form a sealed barrier container;

irradiating the sealed barrier container and its contents with gamma rays; and contacting the sealed barrier container with a vaporized sterilizing agent such as hydrogen peroxide, formaldehyde, peracetic acid, and mixtures of the same.

In one preferred embodiment, a first closed container may be placed within a second container, the second container closed and then placed within the sealable laminate container. Alternatively, multiple inner bags may be "nested" within the next succeeding inner bag in the same manner as the first within the second, so as to form any number of inner bags, with the last inner bag (that contains the preceding inner bags and ultimately the first inner bag) being placed within the sealable laminate container.

The sterile item may be virtually anything required to be maintained in a very sterile condition, and specific examples include culture medium, absorbent wipes and containers of sterilizing solutions; of the last-mentioned class of items, containers of isopropanol and hypochlorite solutions may be specifically mentioned.

The culture medium may be virtually any known culture medium. Typical media are tryptic soy agar-based and containing pancreatic digest of casein, salts, lecithin and a polymeric sorbent, typically having a neutral pH, and being in gel form. Since the end user wishes the culture medium to be supported, it is preferably poured, after steam sterilization, onto a petri dish or a plate and allowed to gel.

In a preferred embodiment, the sterile item is placed into a 1 mil-thick nylon bag, and the bag is closed with closing means, such as a drawstring, stitching, heat sealing or by means of a twist tie, the twist tie being most preferred. In the case of culture medium as the sterile item, a desiccant such as silica gel in a packet is preferably included within the inner bag to absorb moisture. This sterile item-containing inner bag is then either placed within a second inner bag or placed directly into the laminate container. The second inner bag is also preferably a 1 mil gauge nylon bag, and is closed in similar fashion to the first inner bag.

The first inner bag or the second inner bag containing the first inner bag is then placed within a laminate container, also preferably in bag form, the third container comprising a laminate of low density polyethylene and metallized polyester, thereby forming a dustproof and gas- and vapor-impermeable barrier around its contents. This laminate "barrier bag" is also sealed, preferably by heat-sealing, such as by an impulse heat sealer. The laminate preferably comprises a very thin layer, on the order of 0.0002 to 0.0005 mil, metal foil, preferably aluminum "sandwiched" between four layers of polymer; the top two layers preferably comprise 40–50 ga. polyester and 0.5–2.0 mil-thick low density polyethylene, respectively, while the bottom two layers preferably comprise 0.5–1.0 mil-thick low density polyethylene and 1.0–2.0 mil-thick linear low density polyethylene, respectively. Such laminate material is commercially available as "VF-52" from LPS Industries of Newark, N.J. The preferred orientation of the laminate is with the linear low density polyethylene on the inside of the bag and the polyester on the outside. Although the gauge of the laminate material may vary widely, the preferred total thickness that is capable of withstanding chemical attack and yet has sufficient tensile strength is about 3.5 mils.

Following the sealing of the "barrier bag," it and its contents are irradiated with gamma rays. The dosage of gamma irradiation is from about 5 to about 25 kGy, most preferably from about 10 to about 20 kGy.

Finally, immediately prior to usage, the exterior of the "barrier bag" is contacted with the vaporized sterilizing agent, such as a 30% aqueous solution of hydrogen peroxide. The sterilizing agent treatment is conducted at temperatures from 15° to 35° C. for 60 to 90 minutes, and preferably at 99% relative humidity. Two commercially available systems for conducting this last sterilizing step are the Oasys™ system from Amsco Scientific of Apex, N. C., and the la Calhene® system from la Calhene, Inc. of Glen Cove, N.Y.

EXAMPLE

Culture media having the following formula was prepared, steam-sterilized, and poured onto plastic plates and allowed to gel:

pancreatic casein digest 15.0 g
enzymatic soy digest 5.0 g
sodium chloride 5.0 g
lecithin 0.7 g
polysorbate 80 5.0 g
agar 15.0 g
balance water -

A stack of 10 such medium-loaded plates was placed in a 1 mil-thick nylon bag (Capran™ from M & Q Packaging of Philadelphia, Pa.), together with 5.0 g silica gel in a perm-selective packet (MiniPax® from Multisorb Technologies, Inc. of Buffalo, N.Y.). The first bag was closed by means of a twist tie, and then placed within a larger laminate bag made of a 3.5 mils-thick laminate comprising thin foil between four polymer layers as described above, wherein the foil layer was 0.0003 mil-thick, the polyester layer was 48 ga., the first low density polyethylene layer was 1 mil-thick, the second low density polyethylene layer was 0.8 mil-thick, and the linear low density polyethylene layer was 1.5 mils in thickness (VF-52, LPS Industries), and this laminate bag was heat-sealed by an impulse heat sealer.

One hundred such double-bag medium-loaded plates were prepared and packaged in batches of 10 and subjected to various dosages of gamma irradiation within 24 hours. Dosage levels varied from 5.0±1.0 kGy to 20±1.0 kGy; the optimum range of dosage was determined to be 8 to 16 kGy. The exterior of the laminate bags were then subjected to treatment with a sterilizing agent comprising a vaporized mist of a 30% aqueous solution of hydrogen peroxide at 99% relative humidity and at 25° C. for an average time of 75 minutes. The so-packaged and so-treated media-loaded plates were then removed from both bags and used in environmental sterility testing. Prior to such use, however, a number of the samples were evaluated for integrity of packaging by performing a dye migration test, the object of which was to test for possible seal failure due to exposure to relatively high levels of radiation. All samples subjected to the dye migration test showed no seal failure. Thirty of the double-bagged, culture media-loaded plates were removed from the bags and used in environmental sterility testing; all such samples were found to be sterile and successfully cultured both aerobic bacteria and fungal microorganism growth in cleanly separated patterns of each microorganism's characteristic growth pattern.

EXAMPLE 2

Example 1 was repeated with the exception that the first closed bag was placed with a second 1 mil gauge nylon bag of slightly larger dimensions, and the second bag was closed by a twist tie. Both of these inner nylon bags were then placed within the laminate bag, and the same number of batches of such packages were irradiated and contacted with the same vaporized sterilizing agent. Substantially the same sterility test results were observed.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

I claim:

1. A process of storing and maintaining culture medium in a sterile condition comprising the steps:

(a) providing culture medium;

(b) placing said culture medium into at least one inner container;

(c) closing said at least one inner container to form at least one closed inner container;

(d) placing said at least one closed inner container of step (c) into a sealable barrier container comprising a five-layered laminate consisting of an inner layer laminate of two layers of low density polyethylene, an intermediate layer of metal foil and an outer layer laminate consisting of a layer of polyester and a layer of low density polyethylene and sealing the same to form a gas- and vapor-impermeable sealed barrier container;

(e) irradiating said sealed barrier container and its contents with from 5 to 25 kGv of gamma rays;

(f) storing said sealed barrier container; and (g) contacting said sealed barrier container at 15° C. to 35° C. with a vaporized agueous solution of a sterilizing agent immediately prior to opening the same.

2. The process of claim 1 wherein said sealable barrier container contains two inner containers.

3. The process of claim 2 wherein said two inner containers are nylon bags about 1 mil thick.

4. The process of claim 3 wherein said sealable barrier container is in the form of a bag.

5. The process of claim 4 wherein a desiccant is placed in said two inner containers.

6. The process of claim 5 wherein said desiccant is silica gel in a packet.

7. The process of claim 1 wherein said gamma irradiation dosage is from about 10 to about 20 kGy.

8. The process of claim 1 wherein said vaporized sterilizing agent is selected from the group consisting of hydrogen peroxide, formaldehyde, peracetic acid, and mixtures of the same.

9. The process of claim 1 wherein said five-layered laminate of step (d) is about 3.5 mils thick.

10. The process of claim 1 wherein said sealing in step (d) is conducted by heat.

11. The process of claim 1 wherein said culture medium is on an inert support.

12. The process of claim 11 wherein said inert support is a plastic plate.

13. A sealed barrier container stored and maintained by the steps of the process of claim 1.

* * * * *

UNITED STATES PATENT AND TRADEMARK OFFICE
CERTIFICATE OF CORRECTION

PATENT NO : 5,863,496
DATED : January 26, 1999
INVENTOR(S): McElhany

It is certified that error appears in the above-identified patent and that said Letters Patent is hereby corrected as shown below:

Col. 4, line 35: change "kGv" to read --kGy--

Col. 4, line 37: change "agueous" to read --aqueous--

Signed and Sealed this

Ninth Day of May, 2000

Attest:

Q. TODD DICKINSON

Attesting Officer

Director of Patents and Trademarks